United States Patent [19]

Kluge et al.

[11] 4,255,432
[45] Mar. 10, 1981

[54] 8-[2-3-INDOLYL)ETHYL]-1-OXA-3-,8-DIAZASPIRO[4.5]DECAN-2-ONES, PHARMACEUTICAL COMPOSITIONS THEREOF AND METHODS OF USE THEREOF

[75] Inventors: Arthur F. Kluge, Los Altos; Arthur M. Strosberg, Portola Valley; Stefan H. Unger, Palo Alto, all of Calif.

[73] Assignee: Syntex (U.S.A.) Inc., Palo Alto, Calif.

[21] Appl. No.: 72,867

[22] Filed: Sep. 6, 1979

Related U.S. Application Data

[63] Continuation of Ser. No. 9,205, Feb. 5, 1979, abandoned.

[51] Int. Cl.³ ............... A61K 31/435; C07D 521/00; C01D 498/10
[52] U.S. Cl. .................. 424/267; 546/16; 546/19; 546/242; 546/216; 260/319.1; 260/326.16
[58] Field of Search .................. 546/19; 424/267

[56] References Cited

U.S. PATENT DOCUMENTS

| | | | |
|---|---|---|---|
| 3,399,192 | 8/1968 | Regnier et al. | 546/19 |
| 3,555,033 | 1/1971 | Maillard | 546/19 |
| 3,594,386 | 7/1971 | Regnier et al. | 546/19 |

OTHER PUBLICATIONS

Chemical Abstracts, vol. 78 (1973), item 71968t abstracting Maillard in "Chim. Ther." (1972) vol. 7, No. 6, pp. 458–466.

Primary Examiner—Robert T. Bond
Attorney, Agent, or Firm—Tom M. Moran; Alan M. Krubiner

[57] ABSTRACT

Compounds of the formula

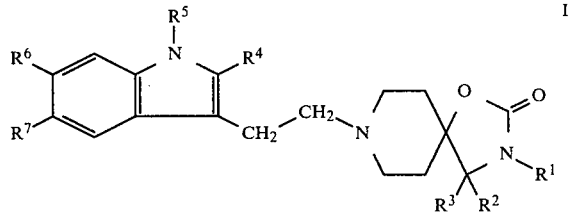

wherein
$R^1$, $R^2$ and $R^3$ are the same or different and are hydrogen, $C_1$ to $C_6$ alkyl, $C_6$ to $C_{12}$ carbocyclic aryl or aralkyl of 1 to 6 carbon atoms in the alkyl moiety and 6 to 12 carbon atoms in the carbocyclic aryl moiety;
$R^4$ and $R^5$ are the same or different and are hydrogen or $C_1$ to $C_6$ alkyl; and
$R^6$ and $R^7$ are the same or different and are hydrogen, $C_1$ to $C_6$ alkyl or $C_1$ to $C_6$ alkoxy. Methods for preparing these compounds are also disclosed. The compounds are useful as antihypertensives and as diuretics. They also function as antihistamines and as bronchodilating agents and are therefore effective in inhibiting the effects of allergic reactions. They are also of use in the treatment of migraine and in the treatment of vasospastic disorders.

11 Claims, 2 Drawing Figures

FIG_1

Intermediate I

+

Intermediate II

↓

I

FIG__2

8-[2-3-INDOLYL)ETHYL]-1-OXA-3-,8-DIAZAS-PIRO[4.5]DECAN-2-ONES, PHARMACEUTICAL COMPOSITIONS THEREOF AND METHODS OF USE THEREOF

This is a continuation of application Ser. No. 9,205, filed Feb. 5, 1979, now abandoned.

FIELD OF THE INVENTION

This invention relates to 8-[2-(3-indolyl)ethyl]-1-oxa-3,8-diazaspiro[4,5]decan-2-ones and pharmaceutically acceptable, nontoxic salts thereof and to methods for preparing these compounds. This invention further relates to 8-[2-(3-indolyl)ethyl]-1-oxa-3,8-diazaspiro[4.5]decan-2-ones optionally substituted at positions 3, 4 and 8 and methods for preparing these compounds. This invention further relates to pharmaceutical compositions comprising one or more of the above compounds and to methods for treating allergic conditions, hypertension, cardiac and vasospastic disorders and migraine in mammals.

DESCRIPTION OF PRIOR ART

Hypertension is a condition in which the pressure of the blood in the arteries is higher than normal. The definition of what is normal depends on the age of the individual, with the normal value increasing with age. The blood pressure for a young adult is about 120/80, the higher figure representing the pressure (in millimeters of mercury) during systole, that is, when the heart is contracting and forcing blood into the arteries. The lower figure is the diastolic blood pressure or the pressure between contractions.

The following are among the drugs presently used to relieve hypertension: diuretics, which increase the excretion of salt and water (thus depleting blood volume), such as the sulfonamides and spironolactones; agents that act directly on the blood vessels to produce dilation such as hydralazine and minoxidil; agents such as guanethidine, bethanidine, debrisoquine and reserpine that produce vasodilitation by counteracting the vasoconstricting action of the sympathetic nervous system; and agents to decrease renin production by the kidney and thus decrease constriction of the blood vessels. Some of the drugs that alter the reninangiotensin system are thought to act in more than one way. This is true of reserpine, for example, and for methyldopa, which also acts through the nervous system. Propanolol may be given in combination with certain of these other drugs in order to counteract their side effects and may have the additional effect of lowering renin output.

Therapy for combatting hypertension usually includes treatment with one or more of the above drugs, often in conjunction with a weight-reducing diet if the patient is overweight. Diets are generally low sodium diets and are rarely considered enjoyable. Many of the drugs are associated with side effects such as weakness or drowsiness and, in some cases, impotence. Multidose, multiple drug therapy plus the side effects of the theraputic agents frequently lead to a lack of compliance with the therapy programs. Therefore there is a need for an effective anti-hypertensive agent exhibiting diminished side-effects and longer duration of action when compared to presently existing agents.

SUMMARY

In summary, the compounds in accordance with the present invention can be represented by the following generic formula:

wherein
R$^1$, R$^2$ and R$^3$ are the same or different and are hydrogen, C$_1$ to C$_6$ alkyl, C$_6$ to C$_{12}$ carbocyclic aryl or aralkyl of 1 to 6 carbon atoms in the alkyl moiety and 6 to 12 carbon atoms in the carbocyclic aryl moiety;
R$^4$ and R$^5$ are the same or different and are hydrogen or C$_1$ to C$_6$ alkyl; and
R$^6$ and R$^7$ are the same or different and are hydrogen, C$_1$ to C$_6$ alkyl or C$_1$ to C$_6$ alkoxy.

Also encompassed within the present invention are the pharmaceutically acceptable, non-toxic salts of the above compounds of formula I.

The process of preparing the compounds of the present invention of formula I comprises treating a compound of the formula wherein R$^4$ and R$^5$ are the same or different and are hydrogen or C$_1$ to C$_6$ alkyl; R$^6$ and R$^7$ are the same or different and are hydrogen, C$_1$ to C$_6$ alkyl or C$_1$ to C$_6$ alkoxy; and X is chloro, bromo or iodo with a compound of the formula:

wherein R$^1$, R$^2$ and R$^3$ are the same or different and are hydrogen, C$_1$ to C$_6$ alkyl, C$_6$ to C$_{12}$ carbocyclic aryl or aralkyl of 1 to 6 carbon atoms in the alkyl moiety and 6 to 12 carbon atoms in the carbocyclic aryl moiety.

The pharmaceutical compositions of the present invention include both solids or powders and solutions comprising one or more of the compounds of the present invention in combination with a suitable pharmaceutical solvent or dispersant, i.e., sterile water or pharmaceutical solid excipients.

The compounds, compositions and methods of the present invention herein before disclosed will become more readily apparent from the following description in connection with the accompanying drawings in which.

DESCRIPTION OF THE PREFERRED EMBODIMENTS

The compounds of the present invention as generally represented by the following formula wherein
$R^1$, $R^2$ and $R^3$ are the same or different and are hydrogen, $C_1$ to $C_6$ alkyl, $C_6$ to $C_{12}$ carbocyclic aryl or aralkyl of 1 to 6 carbon atoms in the alkyl moiety and 6 to 12 carbon atoms in the carbocyclic aryl moiety;

$R^4$ and $R^5$ are the same or different and are hydrogen or $C_1$ to $C_6$ alkyl; and $R^6$ and $R^7$ are the same or different and are hydrogen, $C_1$ to $C_6$ alkyl or $C_1$ to $C_6$ alkoxy. Methods for preparing these compounds are also disclosed. The compounds are useful as antihypertensives and as diuretics. They also function as antihistiminic and bronchodilating agents and are therefore useful in inhibiting the effects of allergic reactions. They are also effective in the treatment of migraine and in the treatment of vasospastic disorders.

The compounds of formula I are preferably as follows:

1. Preferred compounds when $R^1$ is selected from the group hydrogen, methyl, ethyl, i-propyl, n-propyl, n-butyl, phenyl and benzyl.

In the compounds of the present invention of formula I, $R^1$ is preferably selected from the group hydrogen, methyl, ethyl, i-propyl, n-propyl, n-butyl, phenyl and benzyl. In such preferred compounds, $R^2$ and $R^3$ are preferably the same or different and are selected from the group hydrogen and $C_1$ to $C_4$ alkyl, $R^4$ and $R^5$ are the same or different and are selected from the group hydrogen and $C_1$ to $C_4$ alkyl; and $R^6$ and $R^7$ are preferably the same or different and are selected from the group hydrogen, $C_1$ to $C_4$ alkyl and $C_1$ to $C_4$ alkoxy.

(a) In these preferred compounds, most preferred are those where $R^1$ is selected from the group hydrogen, methyl, ethyl, i-propyl, n-butyl, phenyl and benzyl; and $R^2$, $R^3$, $R^4$, $R^5$, $R^6$ and $R^7$ are hydrogen. Such are illustrated by the following compounds:
8-[2-(3-indolyl)ethyl]-1-oxa-3,8-diazaspiro[4.5]decan-2-one;
3-methyl-8-[2-(3-indolyl)ethyl]-1-oxa-3,8-diazaspiro[4.5]decan-2-one; and
3-n-butyl-8-[2-(3-indolyl)ethyl]-1-oxa-3,8-diazaspiro[4.5]decan-2-one.

(b) Other most preferred compounds are those where $R^1$ is selected from the group hydrogen, methyl, ethyl, i-propyl n-butyl, phenyl and benzyl; $R^2$, $R^3$, $R^4$ and $R^7$ are hydrogen; and $R^6$ is methoxy. Such are illustrated by the following compounds:
8-'2-(6-methoxy-2-indolyl)ethyl]-1-oxa-3,8-diazaspiro[4.5]decan-2-one;
3-methyl-8-[2-(6-methoxy-2-indolyl)ethyl]-1-oxa-3,8-diazaspiro[4.5]decan-2-one; and
3-butyl-8-[2-(6-methoxy-2-indolyl)ethyl]-1-oxa-3,8-diazaspiro[4.5]decan-2-one.

(c) Additionally, other most preferred compounds are those where $R^1$ is selected from the group hydrogen, methyl, ethyl, i-propyl, n-butyl, phenyl and benzyl; $R^2$ is selected from the group hydrogen and methyl; $R^3$ is selected from the group methyl, ethyl, phenyl and benzyl; $R^4$ and $R^5$ are methyl; and $R^6$ and $R^7$ are hydrogen. Such are illustrated by the following compounds:
4-ethyl-8-[2-(1,2-dimethyl-3-indolyl)ethyl]-1-oxa-3,8-diazaspiro[4.5]decan-2-one; and
4,4-dimethyl-8-[2-(1,2-dimethyl-3-indolyl)ethyl]-1-oxa-3,8-diazaspiro[4.5]decan-2-one.

(d) Other most preferred compounds are those where $R^1$ is selected from the group hydrogen, methyl, ethyl, i-propyl, n-butyl, phenyl and benzyl; $R^2$, $R^3$, $R^4$ and $R^7$ are hydrogen; and $R^5$ and $R^6$ are methyl.

Such are illustrated by the following:
8-[2-(6,7-dimethyl-3-indolyl)ethyl]-1-oxa-3,8-diazaspiro[4.5]decan-2-one.

(e) Other most preferred compounds are those where $R^1$ is selected from the group hydrogen, methyl, ethyl, i-propyl, n-butyl, phenyl and benzyl; $R^2$, $R^3$ and $R^7$ are hydrogen; and $R^4$, $R^5$ and $R^6$ are methyl. Such are illustrated by the following:
8-[2-(1,2,6-trimethyl-3-indolyl)ethyl]-1-oxa-3,8-diazaspiro[4.5]decan-2-one; and
3-methyl-8-[2-(1,2,6-trimethyl-3-indolyl)ethyl]-1-oxa-3,8-diazaspiro[4.5]decan-2-one.

(f) Other most preferred compounds are those where $R^1$ is selected from the group hydrogen, methyl, ethyl, i-propyl, n-butyl, phenyl and benzyl; $R^3$, $R^4$ and $R^7$ are hydrogen; and $R^2$, $R^5$ and $R^6$ are methyl. Such are illustrated by the following:
4-ethyl-8-[2-(1,6-dimethyl-3-indolyl)ethyl]-1-oxa-3,8-diazaspiro[4.5]decan-2-one; and
3,4-dimethyl-8-[2-(1,6-dimethyl-3-indolyl)ethyl]-1-oxa-3,8-diazaspiro[4.5]decan-2-one.

(g) Other most preferred compounds are those where $R^1$ is selected from the group hydrogen, methyl, ethyl, i-propyl, n-butyl, phenyl and benzyl; $R^2$, $R^3$, $R^4$ and $R^7$ are hydrogen; and $R^5$ and $R^6$ methyl.

Such are illustrated by the following:
4-ethyl-8-[2-(2,6-dimethyl-3-indolyl)ethyl]-1-oxa-3,8-diazaspiro[4.5]decan-2-one.

2. Preferred compounds when $R^2$ and $R^3$ are selected from the group hydrogen, methyl, ethyl, phenyl and benzyl.

In the compounds of the present invention of formula I, $R^2$ and $R^3$ are preferably the same or different and are selected from the group hydrogen, methyl, ethyl, phenyl and benzyl. In such preferable compounds, preferably $R^1$ is selected from the group hydrogen, $C_1$ to $C_4$ alkyl, phenyl and benzyl; $R^4$ and $R^5$ are the same or different and are selected from the group hydrogen and $C_1$ to $C_4$ alkyl; and $R^6$ and $R^7$ are the same or different and are selected from the group hydrogen, $C_1$ to $C_4$ alkyl and $C_1$ to $C_4$ alkoxy.

(a) In these preferred compounds, most preferred are those wherein $R^2$ is selected from the group hydrogen and methyl; $R^3$ is selected from the group methyl, ethyl, phenyl and benzyl; and $R^1$, $R^4$, $R^5$, $R^6$ and $R^7$ are hydrogen. Such are illustrated by the following:

4,4-dimethyl-8-[2-(3-indolyl)ethyl]-1-oxa-3,8-diazaspiro[4.5]decan-2-one; and 4-ethyl-8-[2-(3-indolyl)ethyl]-1-oxa-3,8-diazaspiro[4.5]decan-2-one.

(b) Of the preferred compounds, most preferred are those wherein $R^2$ is selected from the group hydrogen and methyl; $R^3$ is selected from the group methyl, ethyl, phenyl and benzyl; $R^1$ is selected from the group hydrogen, methyl, ethyl, n-propyl, i-propyl, n-butyl, phenyl and benzyl; $R^4$ and $R^5$ are the same or different and are selected from the group hydrogen and $C^1$ to $C^4$ alkyl; and $R^6$ and $R^7$ are the same or different and are selected from the group hydrogen, $C_1$ to $C_4$ alkyl and $C_1$ to $C_4$ alkoxy.

Particularly preferred compounds are those where $R^1$ and $R^7$ are hydrogen; $R^2$ is selected from the group hydrogen and methyl; $R^3$ is selected from the group methyl, ethyl, phenyl and benzyl; $R^4$ and $R^5$ are the same and are methyl; and $R^6$ is methoxy. Such are illustrated by the following:

4-ethyl-8-[2-(1,2-dimethyl-6-methoxy-3-indolyl)ethyl]1-oxa-3,8-diazaspiro[4.5]decan-2-one; and 4,4-dimethyl-8-[2-(1,2-dimethyl-6-methoxy-3-indolyl)ethyl]-1-oxa-3,8-diazaspiro[4.5]decan-2-one.

(c) Additionally, other most preferred compounds are those where $R^2$ is selected from the group hydrogen and methyl; $R^3$ is selected from the group methyl, ethyl, phenyl and benzyl; $R^1$, $R^4$ and $R^7$ are hydrogen; and $R^5$ and $R^6$ are methyl.

(d) Additionally, other most preferred compounds are those where $R^2$ is selected from the group hydrogen and methyl; $R^3$ is selected from the group methyl, ethyl, phenyl and benzyl; $R^1$, $R^4$ and $R^7$ are hydrogen; and $R^5$ and $R^6$ are methyl.

(e) Other most preferred compounds are those where $R^2$ is selected from the group hydrogen and methyl; $R^3$ is selected from the group methyl, ethyl, phenyl and benzyl; $R^1$ and $R^7$ are hydrogen; and $R^4$, $R^5$ and $R^6$ are methyl.

(f) Additionally, other most preferred compounds are those where $R^2$ is selected from the group hydrogen and methyl; $R^3$ is selected from the group methyl, ethyl, phenyl and benzyl; $R^1$ and $R^7$ are hydrogen; and $R^4$, $R^5$ and $R^6$ are methyl.

3. Preferred compounds where $R^4$ is selected from the group hydrogen, methyl, ethyl and i-propyl.

In the compounds of the present invention of formula I, $R^4$ is preferably selected from the group hydrogen, methyl, ethyl and i-propyl. In such preferred compounds, preferably $R^1$ is selected from the group hydrogen, methyl, ethyl, i-propyl, n-propyl, n-butyl, phenyl and benzyl; $R^2$ and $R^3$ are the same or different and are selected from the group hydrogen, methyl, ethyl, phenyl and benzyl; and $R^5$, $R^6$ and $R^7$ are hydrogen. In these preferred compounds, most preferred are those where $R^1$ is selected from the group hydrogen, methyl, ethyl, i-propyl, n-butyl, phenyl and benzyl; $R^2$ is selected from the group hydrogen and methyl; $R^3$ is selected from the group methyl, ethyl, phenyl and benzyl; $R^4$ is methyl; and $R^5$, $R^6$ and $R^7$ are hydrogen. Such are illustrated by the following:

4,4-dimethyl-8-[2-(2-methyl-3-indolyl)ethyl]-1-oxa-3,8-diazaspiro[4.5]decan-2-one;

4-ethyl-8-[2-(2-methyl-3-indolyl)ethyl]-1-oxa-3,8-diazaspiro[4.5]decan-2-one; and 3,4-dimethyl-8-[2-(2-methyl-3-indolyl)ethyl]-1-oxa-3,8-diazaspiro[4.5]decan-2-one.

4. Preferred compounds where $R^5$ is selected from the group hydrogen, methyl, ethyl and i-propyl.

In the compounds of the present invention of formula I, $R^5$ is preferably selected from the group hydrogen, methyl, ethyl and i-propyl. In such preferred compounds, $R^1$ is selected from the group hydrogen, methyl, ethyl, i-propyl, n-propyl, n-butyl, phenyl and benzyl; $R^2$ and $R^3$ are the same or different and are selected from the group hydrogen, methyl, ethyl, phenyl and benzyl; and $R^4$, $R^6$ and $R^7$ are hydrogen. In these preferred compounds, most preferred are those where $R^1$ is selected from the group methyl, ethyl, i-propyl, n-butyl, phenyl and benzyl; $R^2$ is selected from the group hydrogen and methyl; $R^3$ is selected from the group methyl, ethyl, phenyl and benzyl; $R^5$ is methyl and $R^4$, $R^6$ and $R^7$ are hydrogen. Such are illustrated by the following:

3,4-dimethyl-8-[2-(1-methyl-3-indolyl)ethyl]-1-oxa-3,8-diazaspiro[4.5]decan-2-one; and 3,4,4-trimethyl-8-[2-(1-methyl-3-indolyl)ethyl]-1-oxa-3,8-diazaspiro[4.5]decan-2-one.

5. Preferred compounds where $R^6$ and $R^7$ are selected from the group hydrogen, methyl, ethyl, methoxy and ethoxy.

In the compounds of the present invention of formula I, $R^6$ and $R^7$ are preferably the same or different and are selected from the group hydrogen, methyl, ethyl, methoxy and ethoxy; $R^1$, $R^2$ and $R^3$ are the same or different and are selected from the group hydrogen, $C_1$ to $C_4$ alkyl, phenyl and benzyl; and $R^4$ and $R^5$ are the same or different and are selected from the group hydrogen and $C_1$ to $C_4$ alkyl. In such preferred compounds, most preferably $R^6$ and $R^7$ are the same or different and are selected from the group hydrogen, methyl and methoxy; $R^1$ is selected from the group hydrogen, methyl, ethyl, i-propyl, n-propyl, n-butyl, phenyl and benzyl; $R^2$ and $R^3$ are the same or different and are selected from the group hydrogen, methyl, ethyl, phenyl and benzyl; and $R^4$ and $R^5$ are hydrogen. In these preferred and most preferred compounds particularly preferred are the compounds of formula I where $R^1$ is selected from the group hydrogen, methyl, ethyl, i-propyl, n-butyl and benzyl; $R^2$ is selected from the group hydrogen and methyl; $R^3$ is selected from the group methyl, ethyl, phenyl and benzyl; $R^4$ and $R^5$ are hydrogen; and $R^6$ and $R^7$ are methyl. Such are illustrated by the following:

4,4-dimethyl-8-[2-(5,6-dimethyl-3-indolyl)ethyl]-1-oxa-3,8-diazaspiro[4.5]decan-2-one; and 4-ethyl-8-[2-(5,6-dimethyl-3-indolyl)ethyl]-1-oxa-3,8-diazaspiro[4.5]decan-2-one.

The preferred pharmaceutically acceptable salts are hydrogen addition salts of bromide, sulfate, lactate, tartrate, succinate and especially chloride and maleate. Thus, the preferred salts are the preferred anion addition salts of formula I and correspondingly the particularly preferred salts are the preferred hydrogen-anion addition salts of the preferred and particularly preferred compounds of formula I and especially the hydrochloride and maleate salts.

Figure 1:
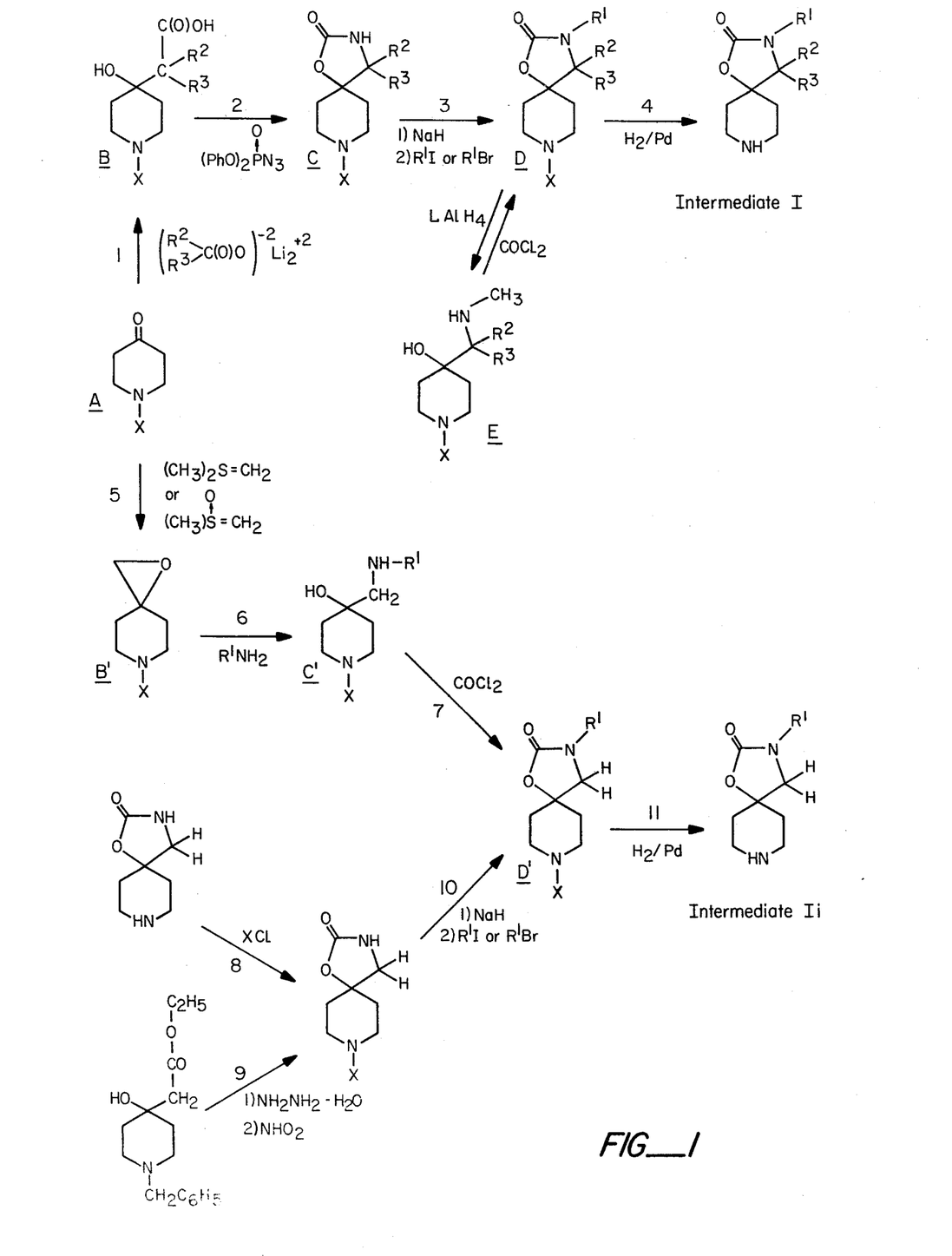
FIG. 1 is a reaction sequence illustrative of the preparation of the intermediate compounds of the present invention.

Referring now to FIG. 1, the intermediate compounds useful in the preparation of the compounds of formula I are prepared by first treating (step 1.) N-carbobenzyloxy- or N-benzyl-4-piperidone, compound A, dissolved or dispersed in an inert solvent with a alkali metal salt of an $R^2$,$R^3$-substituted carboxylic acid, typically a lithium salt, in an inert atmosphere, at $-70°$ to −75° for a time sufficient to complete the reaction, typically 5 minutes to 5 hours. Mole ratios of the alkali metal salt:N-substituted piperidone range from 1:5 to 5:1, preferably 1:1. The resulting (N-protected 4-hydroxypiperidin-4-yl)-$R^2$,$R^3$-substituted acetic acid, compound B, is next treated (step 2.) with diphenylphosphoryl azide in a modification of the Curtius Rearrangement, forming the (not isolated) acyl azide, which, after thermal rearrangement to the isocyanate, cyclizes to form a 4,4-$R^2$,$R^3$-disubstituted-8-carbobenzyloxy- or -benzyl-1-oxa-3,8-diazaspiro[4.5]-decan-2-one, Compound C. This Rearrangement is a well-known prior art technique and has been described with particularity in, for example, Lebel, et al, *Synthesis,* 1973, 678.

The N-protected 1-oxa-3,8-diazaspiro[4.5]decan-2-one (Compound C) is reacted with an alkali metal hydride (step 3.1). This initial treatment is typically conducted at temperatures in the range of from about −30° to 30°, preferably from about −10° to 5° from about one minute to one hour, preferably from about five minutes to 20 minutes. An $R^1$ halide such as an alkyl chloride, bromide, or iodide typically dissolved in an inert organic solvent, is then added to the preceding mixture (step 3.2). Typically, this treatment is conducted at temperatures in the range of from about 25° to 45°, for from about one minute to three hours, preferably from about 10 to 30 minutes. Typically, mole ratios of alkali metal hydride:diazaspirodecanone of from about 1 to 5:1, preferably from about 1.0 to 1.3:1 are used, with mole ratios of compound C:$R^1$ halide being in the range of from about 1 to 5:1 preferably from about 1.0 to 1.3:1. Suitable alkali metal hydrides which can be used include, for example, sodium hydride, potassium hydride, lithium hydride and the like. Suitable inert organic solvents which can be used include, for example, tetrahydrofuran, dioxane, dimethoxyethane, dimethylformamide and the like, and mixtures thereof. Both procedures of the treatment are conducted under anhydrous conditions, and preferably under an inert atmosphere (e.g. nitrogen). Compound D is preferably isolated before being used as starting material for the next step. Such isolation can be effected by conventional separation procedures such as, for example, precipitation with water, extraction, crystallization or chromatography. Specific illustrations of typical separation and isolation procedures can be had by reference to the appropriate Preparations, hereinbelow.

Intermediate I is formed from compound D by catalyzed hydrogenolysis (in such case, when X is benzyl, $R^1$ cannot be aralkyl and $R^2$ and/or $R^3$ cannot be carbocyclic aryl), step 4. Typically this reaction is carried out in an inert solvent at elevated pressures and temperatures, 20-100 psi and 30°-100°, preferably 55-65 psi and 45°-55°, for a time sufficient to complete the reaction, 10 minutes to 5 hours, typically 1 hour. When catalyzed hydrogenation is employed, any of the recognized metallic or metal oxide-supported or unsupported catalysts can be used, including platinum, platinum oxide and palladium. Preferably palladium on carbon is used in the catalyzed reaction. Various inert solvents useful in the reduction include both polar and non-polar solvents such as the alcohols illustrated by methanol, ethanol and the like, the ethers illustrated by diethyl ether, dioxane and the like, and the esters illustrated by ethyl acetate and the like.

Intermediate I is readily isolated from the reaction mass by any of the conventional methods indicated above.

As an alternate procedure for the preparation of Intermediate Ii(Intermediate I where $R^1 = R^2 =$ hydrogen), trimethyl sulfonium or trimethyl sulfoxonium iodide is first treated with an alkali metal hydride thereby abstracting a proton from one methyl group and forming the "ylid". Compound A, dispersed or dissolved in a suitable organic liquid, is added to the resulting reaction mixture (step 5) typically at about 0°-60° and, after a time sufficient to complete the reaction, usually 1 hour to 48 hours, the N-protected piperidine epoxide, compound B', is obtained. The epoxide ring is readily opened at elevated temperature by any R'-substituted amine (step C) forming a 1-carbobenzyloxy- or 1-benzyl-4-hydroxy-4-(R'aminomethyl)-piperidine, Compound C'. Typical temperatures for such ring-opening reaction include 100°-200°, usually 150°-170°. The reaction is typically conducted in the absence of solvent. Compound C' is then treated with phosgene (step 7) in the presence of a suitable acid acceptor, thereby forming 3-R'-8-X-1-oxa-3,8-diazaspiro[4.5]decan-2-one, compound D'. This latter compound can be converted to Intermediate Ii by the hydrogenation process (step 11) described previously for compound D. As noted before in cases where $R^1$ is aralkyl, the blocking group X must be the radical carbobenzyloxy.

As an alternate technique for the preparation of the immediate precursor to Intermediate Ii, compound D' can be prepared by treating 8-benzyl- or 8-carbobenzyloxy-1-oxa-3,8-diazaspiro[4.5]decan-2-one with an alkali metal hydride (Step 10.1) followed by a $R^1$ bromide or iodide (step 10.2) in a manner identical to that described above for the treatment of compound C (step 3.). FIG. 1 illustrates the preparation of this compound by two alternate routes, i.e., from 1-oxa-3,8-diazaspiro[4.5]-decan-2-one (step 8) and from ethyl (1-benzyl-4-hydroxy-piperidine-4-yl)acetate (step 9). See Preparations 8 and 9 respectively. Reduction of compound D (X=benzyl, $R^1$=H, $R^2$ and $R^3$=H or alkyl) with lithium aluminum hydride affords compound E. Typically, this reduction is accomplished at elevated temperatures, in an inert organic solvent, for example at 30°-100° in tetrahydrofuran, for a time sufficient to complete the reaction. Treatment of E with phosgene or diphenyl carbonate gives compound D ($R^1$=methyl). This reaction is conducted effectively at temperatures from 10° to 50°, preferably 20° in an inert organic solvent such as dichloromethane.

Figure 2:
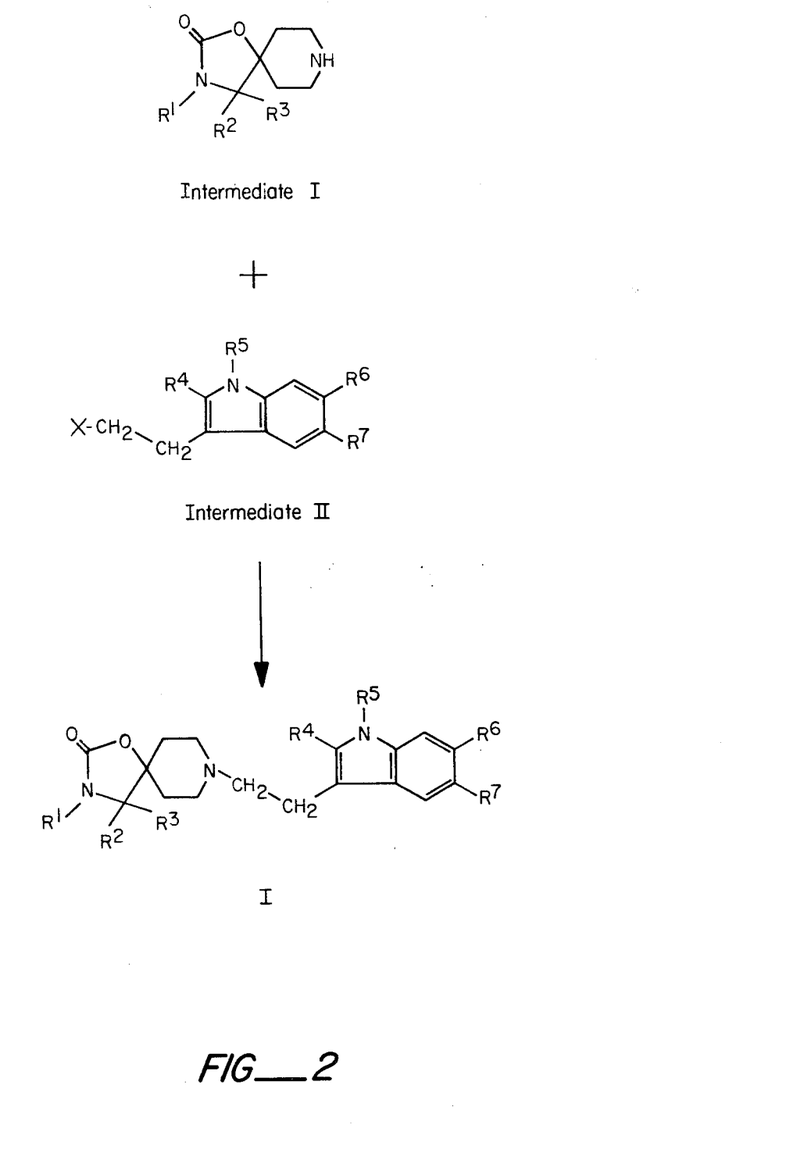
FIG. 2 is a reaction sequence illustrative of the preparation of the compounds of the present invention of formula I.

Referring now to FIG. 2, the compounds of the present invention of formula I can be conveniently prepared by treating the 3-(2-haloethyl)indolyl compounds, Intermediate II with the compounds, Intermediate I. Typically, this treatment is conducted in the presence of an acid acceptor in an inert organic solvent at temperatures in the range of from about −10° to 120°, preferably from about 50° to 100°, for from about six hours to 48 hours, preferably from about 16 to 18 hours. Compounds capable of interacting with the hydrogen halide by-product of the reaction are effective acid acceptors. Such compounds useful in facilitating the reaction are familiar to one skilled in the art and include a variety of organic and inorganic bases that do not interfere with the displacement reaction of Intermediates I and II. Typically bases such as the trialkylamines, e.g. triethylamine, quinuclidine, etc. and the alkali metal carbonates, e.g. potassium carbonate, sodium carbonate, etc. are useful for this purpose. Typically, a mole ratio of Intermediate I:Intermediate II in the range of from about 1:1 to 3:1, preferably from about 1:1, is used. Suitable inert organic solvents which can be used include, for example, methanol, ethanol, dimethylformamide, tetrahydrofuran, dimethylsulfoxide, tolene and the like and mixtures thereof. The resulting products of formula I can then be separated and isolated according to conventional procedures such as, for example, evaporation, crystallization, column chromatography, thin-layer chromatography, etc. Specific illustrations of typical separation and isolation procedures can be had by reference to the corresponding Examples set forth hereinbelow.

The 3-(2-haloethyl)indolyl intermediate, Intermediate II, may be readily prepared by a variety of techniques. In one embodiment for example, a solution or dispersion of the substituted, partially substituted or unsubstituted $R^4$, $R^5$, $R^6$, $R^7$-3-(2-hydroxyethyl)indole is treated with a phosphorous trihalide, a triphenyl phosphine halogen adduct or a triphenoxyphosphorous alkyl halide to yield the $R^4$, $R^5$, $R^6$, $R^7$-3-(2-haloethyl)indole. This is a prior art technique is well known to those skilled in the art. See for example J. Org. Chem. 26, 3645 (1961); J. Amer. Chem. Soc. 86, 2093 (1964); and J. Chem. Soc. (1953) 224. The reaction is typically carried out in an inert reaction medium at from about room temperature to about 100° using an excess of halogenating agent, e.g. 1.1 to 3.0 times the stoichiometric amount actually required. Appropriate reaction media include for example, dimethylformamide, diethyl ether and the like. The haloethylindole intermediate is preferably isolated before being used in the reaction with Intermediate I, such being accomplished by conventional processes as set forth above. These reactions are described with particularity in Preparations 12 and 13.

Additionally, substitutions at the group $R^5$ or at position 1 of the indole nucleus may be carried out by the prior art techniques of alkylation of 3-(2-hydroxyethyl)indole using an alkyl indole in liquid ammonia. See Preparation 11.

The compounds of the invention are also useful in the treatment of cardiac disorders in mammals. They are similarly effective as antihistimines. In addition they display bronchodilating activity and are therefore effective as antiasthmatics. They are also effective in the treatment of migraine as well as vasospastic disorders.

For the treatment of allergies (antihistiminic or bronchodilating effects, cardiac disorders, hypertension, migraine and vasospastic disorders the compounds of this invention are typically administered in dosages of about from 0.01 to 5 mg per kg. of body weight. The precise effective dosage will, of course, vary depending upon the mode of administration, the condition being treated and the host. Where the compounds are used to treat cardiac conditions, the compounds are typically administered either orally or intravenously. Where the compounds are administered to treat hypertension, migraine and vaospastic disorders the compounds are, for the sake of convenience, typically administered orally. Where used for the treatment of allergies, particularly asthma, they are administered nasally as a fine spray or aerosol or orally.

The compounds of the invention can be administered for the treatment of asthma, vascular disorders and hypertension in a wide variety of dosage forms, either alone or in combination with other pharmaceutically compatible medicaments, in the form of pharmaceutical compositions suited for nasal, oral or parenteral administration. The compounds are typically administered as pharmaceutical compositions consisting essentially of the compounds of the invention and a pharmaceutical carrier. In the case of the compounds of formula I, the compounds are typically administered as pharmaceutically acceptable salts. The pharmaceutical carrier can be either a solid material or liquid in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, pharmaceutical phosphate salts and the like.

The liquid compositions can, for example, be in the form of solutions, emulsions, suspensions, syrups or elixirs and optionally can contain small quantities of preservatives and/or buffering agents and preferably contain the therapeutic agent in convenient unit dosage concentrations.

The solid compositions can take the form of tablets, powders, capsules, pills and the like, preferably in unit dosage forms for simple administration or precise dosages. Suitable solid carriers include, for example, pharmaceutical grades of starch, lactose, sodium saccharine, sodium bisulfite and the like.

In the compounds of formula I where $R^2$ is not the same as $R^3$ a chiral center is present. These compounds can be administered as racemic mixtures or they can be administered as resolved enantiomers or optical isomers. In some instances, one enantiomer or optical isomer exhibits a greater physiological effect than does the other corresponding enantiomer or optical isomer.

As used in the specification and the appended claims, the following terms have the meaning indicated. The term "$C_1$ to $C_6$ alkyl" refers to a straight or branched chain monovalent substituent consisting solely of carbon and hydrogen, containing no unsaturation, and having from 1 to 6 carbon atoms. Examples of such alkyl groups are methyl, ethyl, n-propyl, i-propyl, n-butyl, t-butyl, n-hexyl, and the like. The term "$C_1$ to $C_6$ alkoxy" refers to the above 1 to 6 carbon-containing alkyl groups linked through an ether linkage, having the free valence from the ether oxygen. Examples of such groups include methoxy, ethoxy, n-propoxy, i-propoxy, n-butoxy, t-butoxy, n-hexyloxy, and the like. The term "halo" refers to fluoro, chloro, bromo and iodo. "$C_6$ to $C_{12}$ carbocyclic aryl" is intended to mean the monovalent aromatic cyclic (including polycyclic) compounds consisting of solely carbon and hydrogen and having at least 6 carbon atoms in the ring, such as the group phenyl, and up to 12 ring carbon atoms. The term "aralkyl of 1 to 6 carbon atoms in the alkyl moiety and 6 to 12 carbon atoms in the carbocyclic aryl moiety" is defined as 1 to 6 carbon-containing alkyl groups (some of which are defined above) attached to a monocyclic or polycyclic aromatic ring or rings of 6 to 10 carbon atoms which are optionally substituted with one or two $C_1$ to $C_6$ alkyl groups. Illustrative of such are the groups $PhCH_2$—, $PhCH_2CH_2$—, $NaphCH_2CH_2$ and $NaphCH_2CH$— where Ph and Naph are phenyl and naphthyl respectively.

The term "pharmaceutically acceptable, non-toxic salts" is recognized in the art to designate addition salts formed from an acid that is physiologically innocuous when administered in a dosage and at an interval that is effective for the indicated therapeutic use of the parent compound. Typical pharmaceutically acceptable addition salts of the compounds of formula I include salts with inorganic acids such as hydrochloric acid, hydrobromic acid, sulfuric acid, nitric acid or phosphoric acid; and salts with organic acids such as acetic acid, propionic acid, lactic acid, succinic acid, malic acid, maleic acid, tartaric acid, citric acid, and the like.

As noted previously, the compounds of formula I possess a chiral center when $R^2$ and $R^3$ are different. Accordingly, these compounds of the invention may be prepared in either their optically active form or as a racemic mixture. Unless otherwise specified, the compounds described herein are all in the racemic form. However, the scope of the subject invention is not to be considered limited to the racemic form, but to encompass the individual optical isomers of the compounds of the present invention.

Where desired, the individual optically isomeric compounds can be isolated by conventional separation and purification procedures by conventional resolution procedures (for example, by reacting the optically isomeric mixtures with an optically active acid affording a mixture of optically isomeric salts of the compounds of formula I which can be resolved by conventional procedures, e.g., crystallization into the respective (+) and (−) optically isomeric salts). Optimum physical or physical-chemical separation and resolution procedures can be obtained by routine trial and error techniques well within the scope of those skilled in the art.

A further understanding of the invention can be had from the following non-limiting Preparations and Examples. As used hereinabove and below unless expressly stated to the contrary, all temperatures and temperature ranges refer to the Centigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that Preparation or Examples in the terms of moles of finite weight or volume. As noted earlier, compounds having assymetric centers and optical activity are isolated in their racemic form (±) unless otherwise indicated.

PREPARATION 1

1. To a 100 ml flask maintained under argon are added 2.22 g diisopropylamine and 15 ml tetrahydrofuran. The contents of the flask are cooled to 0° and are maintained at that temperature. A solution of 1.5 M n-butyllithium (14.7 ml) is added and the solution is stirred for five minutes. Isobutyric acid (0.88 g) is added and the mixture is stirred for 15 minutes at 20°. The mixture is cooled to −70° and a solution of 2.33 g of N-carbobenzyloxy-4-piperidone in 5 ml tetrahydrofuran is added at such a rate that the temperature remains below −50°. The mixture is allowed to warm to room temperature and is poured into 150 ml diethyl ether. This solution is extracted with two 150 ml portions of 1 N hydrochloric acid, 50 ml of water and 100 ml of 2% sodium hydroxide. The basic layer is acidified with 10 N hydrochloric acid and the resulting mixture is extracted with three 50 ml portions of diethyl ether. Evaporation of the ether affords an oil which is triturated with 50 ml hexane to give 1.65 g 2-(1-carbobenzyloxy-4-hydroxypiperidin-4-yl)-2-methylpropionic acid, an oil.

Similarly prepared are the following:
(from phenylacetic acid),
(1-carbobenzyloxy-4-hydroxypiperidin-4-yl)phenylacetic acid, an oil; and
(from 3-phenylpropionic acid),
2-(1-carbobenzyloxy-4-hydroxypiperidin-4-yl)-3-phenylpropionic acid, mp 166°–168.5°.

2. A mixture of 2.12 g diisopropylamine and 15 ml tetrahydrofuran is stirred under argon at 0°. To this solution is added over two minutes 14 ml of 1.5 M n-butyllithium. To this solution at 0° is added 0.6 g acetic acid. The mixture is stirred five minutes at 20° and then cooled to −70°. To this mixture is added a solution of 1.89 g N-benzyl-4-piperidone in 4 ml tetrahydrofuran. The mixture is allowed to warm to room temperature and poured into 50 ml 1% sodium hydroxide. This mixture is extracted with three 50 ml portions of diethyl ether. The aqueous phase is adjusted to pH 7.0 with 3 N hydrochloric acid and is extracted with five 40 ml portions of dichloromethane. Evaporation of the dichloromethane affords (1-benzyl-4-hydroxypiperidin-4-yl)acetic acid.

Similarly prepared are the following:
(from propionic acid),
2-(1-benzyl-4-hydroxypiperidin-4-yl)propionic acid;
(from butyric acid),
2-(1-benzyl-4-hydroxypiperidin-4-yl)butyric acid;
(from pentanoic acid),
2-(1-benzyl-4-hydroxypiperidin-4-yl)pentanoic acid; and
(from isobutyric acid),
2-(1-benzyl-4-hydroxypiperidin-4-yl)-2-methylpropionic acid.

PREPARATION 2

A mixture of 2-(1-carbobenzyloxy-4-hydroxypiperidin-4-yl)-2-methylpropionic acid, 1.29 g diphenylphosphoryl azide, 0.47 g triethylamine and 50 ml toluene is heated at reflux for 18 hours. Evaporation of solvent gives a residue which is taken up in 125 ml dichloromethane and is washed with 50 ml 1 N hydrochloric acid and 50 ml, 5% sodium bicarbonate. Evaporation of the solvent followed by trituration with diethyl ether affords 1.86 g 4,4-dimethyl-8-carbobenzyloxy-1-oxa-3,8-diazaspiro[4.5]decan-2-one, mp 208°–209°.

Similarly prepared are the following:
4-phenyl-8-carbobenzyloxy-1-oxa-3,8-diazaspiro[4.5]decan-2-one, mp 168°–169°; and
4-benzyl-8-carbobenzyloxy-1-oxa-3,8-diazaspiro[4.5]decan-2-one, mp 119°–121°.

PREPARATION 3

1. A mixture of 16.5 g 8-benzyl-1-oxa-3,8-diazaspiro[4.5]decan-2-one, 6.6 g, 50% suspension of sodium hydride in mineral oil, 15 g ethyl iodide and 70 ml N,N-dimethylformamide is heated at 90° for one hour. The mixture is poured into 150 ml water and the resulting mixture acidified with 10 N hydrochloric acid. The mixture is extracted with two 100 ml portions of hexane. The aqueous layer is basified with sodium hydroxide and extracted with three 75 ml portions of dichloromethane. Removal of solvent in vacuum affords a residue which when crystallized from heptane gives 3-ethyl-8-benzyl-1-oxa-3,8-diazaspiro[4.5]decan-2-one, mp 105°–106°.

Similarly prepared are the following:
(from methyl iodide),
3-methyl-8-benzyl-1-oxa-3,8-diazaspiro[4.5]decan-2-one, mp 137°–138°;
(from 1-bromopropane),
3-n-propyl-8-benzyl-1-oxa-3,8-diazaspiro[4.5]decan-2-one, mp 98°–99°;
(from 2-bromopropane), 3-isopropyl-8-benzyl-1-oxa-3,8-diazaspiro[4.5]decan-2-one, mp 120°–121°;
(from 4-bromobutane),
3-n-butyl-8-benzyl-1-oxa-3,8-diazaspiro[4.5]decan-2-one, mp 80.5°–81°; and
(from 2-bromoethylbenzene),
3-(2-phenethyl)-8-benzyl-1-oxa-3,8-diazaspiro[4.5]decan-2-one, mp 155°–157°.

2. A mixture of 9.1 g 8-carbobenzyloxy-1-oxa-3,8-diazaspiro[4.5]decan-2-one, 1.85 g, 57% suspension of sodium hydride in mineral oil, 6 ml methyl iodide and 45 ml N,N-dimethylformamide is heated one hour at 60°. The mixture is poured into 200 ml water and the resulting mixture extracted with three 100 ml portions of dichloromethane. The dichloromethane extracts are combined and evaporated to give a residue which is washed with three 100 ml portions of hexane and three 100 ml portions of water. This affords 8.95 g of 3-methyl-8-carbobenzyloxy-1-oxa-3,8-diazaspiro[4.5]decan-2-one, an oil; m/e=304 (M+).

Similarly prepared is (from benzyl bromide) 3-benzyl-8-carbobenzyloxy-1-oxa-3,8-diazaspiro[4.5]decan-2-one, an oil; m/e=380 (M+).

PREPARATION 4

1. A mixture of 4.54 g 4,4-dimethyl-8-carbobenzyloxy-1-oxa-3,8-diazaspiro[4.5]decan-2-one, 75 ml ethanol and 1 g 5% palladium on carbon is hydrogenated at 60 psi and 50° for one hour. Filtration and evaporation affords 2.65 g 4,4-dimethyl-1-oxa-3,8-diazaspiro[4.5]decan-2-one, mp 238°–240°.

Similarly prepared are the following:
4-phenyl-1-oxa-3,8-diazaspiro[4.5]decan-2-one, mp 38°–40°; and
4-benzyl-1-oxa-3,8-diazaspiro[4.5]decan-2-one, mp 237°–238°.

2. A mixture of 22.2 g 3-benzyl-8-carbobenzyloxy-1-oxa-3,8-diazaspiro[4.5]decan-2-one, 150 ml ethanol and 5 g, 5% palladium on barium sulfate is hydrogenated at 60 psi at room temperature for 90 minutes. After filtration and removal of solvent there is obtained 15.4 g of 3-benzyl-1-oxa-3,8-diazaspiro[4.5]decan-2-one, mp 69°–71°.

3. A mixture of 6.2 g 8-benzyl-1-oxa-3,8-diazaspiro[4.5]decan-2-one, 50 ml ethanol and 0.5 g, 10% palladium on carbon is hydrogenated at 60 psi and 50° for 18 hours. After filtration and removal of solvent there is obtained 4.2 g 1-oxa-3,8-diazaspiro[4.5]decan-2-one, mp 158°–161°.

Similarly prepared are the following:
3-methyl-1-oxa-3,8-diazaspiro[4.5]decan-2-one, mp 95°–96°;
3-ethyl-1-oxa-3,8-diazaspiro[4.5]decan-2-one, mp 55°–57°;
3-n-propyl-1-oxa-3,8-diazaspiro[4.5]decan-2-one, oil;
3-isopropyl-1-oxa-3,8-diazaspiro[4.5]decan-2-one, mp 41°–45°;
3-n-butyl-1-oxa-3,8-diazaspiro[4.5]decan-2-one, oil; and
3-(2-phenethyl)-1-oxa-3,8-diazaspiro[4.5]decan-2-one, mp 93°–95°.

PREPARATION 5 a. In a 250 ml flask under argon are mixed 1.2 g mineral oil-free sodium hydride, 11 g trimethylsulfoxonium iodide and 60 ml dimethylsulfoxide. The mixture is stirred for two hours and then is added 9.32 g N-carbobenzyloxy-4-piperidone, the stirring being continued at room temperature for 30 minutes, followed by 50° for one hour, then room temperature for 18 hours. The mixture is poured into 300 ml water and extracted with three 70 ml portions of diethyl ether. The combined diethyl ether extracts are washed with 50 ml water. Removal of solvent by evaporation affords 3.8 g of crude epoxide.

b. The product of step a. is mixed with 5 g of aniline and the mixture is heated at 160° for four hours. This mixture is cooled to room temperature and is dissolved in 150 ml diethyl ether. The ether solution is extracted with two 40 ml portions of 1 N hydrochloric acid. The acid extract is basified with 20% sodium hydroxide and the resulting mixture is extracted with three 50 ml portions of diethyl ether. Removal of the ether by evaporation yields a crude product which is filtered through 50 g silica gel with 150 ml, 40% diethyl ether-hexane, followed by 150 ml diethyl ether. Evaporation of the diethyl ether filtrate gives 2.2 g of 1-carbobenzyloxy-4-hydroxy-4-anilinomethylpiperidine, an oil, m/e=340.

Similarly prepared are the following:
(from 2-methoxyaniline),
1-carbobenzyloxy-4-hydroxy-4-(2-methoxyanilino)methylpiperidine;
(from 3-methoxyaniline),
1-carbobenzyloxy-4-hydroxy-4-(3-methoxyanilino)methylpiperidine; and
(from 4-chloroaniline),
1-carbobenzyloxy-4-hydroxy-4-(4-chloroanilino)methylpiperidine.

PREPARATION 6

To a mixture of 2.2 g 1-carbobenzyloxy-4-hydroxy-4-anilinomethylpiperidine, 3 ml triethylamine and 20 ml dichloromethane is added a solution of 3 g phosgene in 25 ml toluene. After 30 minutes the mixture is washed with 100 ml, 1 N hydrochloric acid. Removal of solvent by evaporation followed by recrystallization from diethyl ether-hexane affords 1.2 g of 3-phenyl-8-carbobenzyloxy-1-oxa-3,8-diazaspiro[4.5]decan-2-one, mp 100°–102°.

Similarly prepared are the following:
3-(2-methoxyphenyl)-8-carbobenzyloxy-1-oxa-3,8-diazaspiro[4.5]decan-2-one;
3-(3-methoxyphenyl)-8-carbobenzyloxy-1-oxa-3,8-diazaspiro[4.5]decan-2-one; and
3-(4-chlorophenyl)-8-carbobenzyloxy-1-oxa-3,8-diazaspiro[4.5]decan-2-one.

PREPARATION 7

A mixture of 3.4 g 3-phenyl-8-carbobenzyloxy-1-oxa-3,8-diazaspiro[4.5]decan-2-one, 50 ml ethanol and 0.4 g, 10% palladium on carbon is hydrogenated at room temperature and 60 psi for 6 hours. Filtration and removal of solvent affords 2.45 g 3-phenyl-1-oxa-3,8-diazaspiro[4.5]decan-2-one, a pasty solid; m/e=232 (M+).

Similarly prepared are the following:
3-(2-methoxyphenyl)-1-oxa-3,8-diazaspiro[4.5]decan-2-one;
3-(3-methoxyphenyl)-1-oxa-3,8-diazaspiro[4.5]decan-2-one; and
3-(4-chlorophenyl)-1-oxa-3,8-diazaspiro[4.5]decan-2-one.

PREPARATION 8

To a mixture of 9.5 g 1-oxa-3,8-diazaspiro[4.5]decan-2-one and 75 ml water, at 0°, is added 6.3 g sodium bicarbonate and 10.9 g benzyl chloroformate. The mixture is stirred 18 hours at 0°, acidified with 10 N hydrochloric acid and stirred four hours at room temperature. The mixture is extracted with three 50 ml portions of dichloromethane. Removal of solvent affords 14.4 g 8-carbobenzyloxy-1-oxa-3,8-diazaspiro[4.5]decan-2-one, mp 126°–128°.

PREPARATION 9 a. A mixture of ethyl (1-benzyl-4-hydroxypiperidin-4-yl)acetate [Helv. Chim. Acta, 51, 1184 (1958)] and 25 ml hydrazine hydrate is heated at reflux for ten minutes. 150 ml Ethanol is added and the reflux continued one hour. The solvent is removed at reduced pressure, the residue taken up in 100 ml ethanol and this solution mixed with 100 ml diethyl ether. Crystals deposit upon cooling. Filtration affords 20.8 g of the hydrazide, mp 160°–161.5°.

b. To 20.8 g of (1-benzyl-4-hydroxypiperidin-4-yl)acetic acid hydrazide (step a.) in 120 ml water is added sufficient 10 N hydrochloric acid until the solution remains acid to litmus and the solid dissolves. The resulting solution is cooled to 10° and a solution of 6.3 g sodium nitrite in 60 ml water is added over five minutes. The solution is stirred five minutes at 10° and twenty minutes at 60°. The solution is saturated with sodium chloride and is then basified with 20% sodium hydroxide. Filtration affords 16.7 g 8-benzyl-1-oxa-3,8-diazaspiro[4.5]decan-2-one, mp 181°–182°.

PREPARATION 10 a. To a stirred mixture of 7 g lithium aluminum hydride and 150 ml tetrahydrofuran under argon is added dropwise over 20 minutes a solution of 24.6 g 8-benzyl-1-oxa-3,8-diazaspiro[4.5]decan-2-one in 150 ml tetrahydrofuran. The mixture is heated at reflux for two hours. The stirred mixture is treated with sequential dropwise additions of 7 ml water, 7 ml 15% sodium hydroxide and 21 ml water. The mixture is filtered and the filter cake is washed with three 200 ml portions of dichloromethane. Evaporation of the combined filtrates affords 23 g of 1-benzyl-4-hydroxy-4-methylaminomethylpiperidine, an oil.

b. A solution of 23 g 1-benzyl-4-hydroxy-4-methylaminomethylpiperidine and 250 ml dichloromethane is mixed with 100 ml of a 15% solution of phosgene in toluene. Evaporation of solvent gives a residue which is treated with 300 ml dichloromethane and 300 ml aqueous sodium bicarbonate. Separation of the dichloromethane layer followed by evaporation gives 20 g 3-methyl-8-benzyl-1-oxa-3,8-diazaspiro[4.5]decan-2-one, mp 137°–138°.

PREPARATION 11

To a solution of sodium amide from 0.63 g sodium in 50 ml liquid ammonia is added in dropwise fashion a solution of 3.22 g of 3-(2-hydroxyethyl)indole in 10 ml diethyl ether. After stirring 10 minutes a solution of 1.37 ml methyl iodide in 1.5 ml diethyl ether is added in one portion. The mixture is stirred for 15 minutes and then the ammonia is allowed to evaporate. The residue is mixed with 100 ml water and is extracted into 200 ml diethyl ether. The organic phase is separated and is dried over magnesium sulfate. Filtration and evaporation affords 3.64 g of 1-methyl-3-(2-hydroxyethyl)indole, an oil.

Similarly prepared are the following:
(from ethyl iodide),
1-ethyl-3-(2-hydroxyethyl)indole;
(from propyl iodide),
1-propyl-3-(2-hydroxyethyl)indole; and
(from butyl iodide),
1-butyl-3-(2-hydroxyethyl)indole.

PREPARATION 12

A mixture of 3.64 g 1-methyl-3-(2-hydroxyethyl)indole, 18 g methyltriphenoxyphosphonium iodide (J.O.C. 35 2323) and 75 ml dry N,N-dimethylformamide is stirred 2.5 hours at room temperature. Then 5 ml methanol are added, and the mixture is stirred 30 minutes. The mixture is poured into 500 ml dichloromethane and is washed successively with 50 ml portions of 5% aquous sodium thiosulfate, 10% NaOH, and water. The organic layer is dried briefly over magnesium sulfate and most of the solvent removed by evaporation, affording 1-methyl-3-(2-iodoethyl)indole.

Similarly prepared are the following:
(from 1-ethyl-3-(2-hydroxyethyl)indole),
1-ethyl-2-(2iodoethyl)indole; and
(from 1-butyl-3-(2-hydroxyethyl)indole),
1-butyl-3-(2-iodoethyl)indole.

PREPARATION 13

To a mechanically stirred mixture of 18.3 g (69.7 mmol) triphenylphosphine and 200 ml acetonitrile, 11.15 g (69.7 mmol) bromine is added dropwise over 20 minutes. The mixture is stirred 20 minutes at 0° and the ice bath is removed. A solution of 12.1 g (63.4 mmol) 6-methoxy-3-(2-hydroxyethyl)indole in 60 ml acetonitrile is added over 30 minutes. After stirring 2 hours at room temperature the mixture is diluted with 250 ml diethyl ether. The liquid is decanted from precipitated tar. The residue is washed with an additional 250 ml diethyl ether. The volume of the ethereal extracts is reduced to about 60 ml and the solution is filtered through 75 g silica gel with diethyl ether. The solvent is removed to yield 6-methoxy-3-(2-bromoethyl)indole, 4.1 g, yellow waxy solid, mp 98°–101°, which turns green on standing.

Similarly prepared are the following:
(from 6-ethoxy-3-(2-hydroxyethyl)indole),
6-ethoxy-3-(2-bromoethyl)indole; and
(from 6-isopropoxy-3(2-hydoxyethyl)indole),
6-isopropoxy-3-(2-bromoethyl)indole.

EXAMPLE 1

A mixture of 3.94 g of 3-(2-bromoethyl)indole, 2.74 g of 1-oxa-3,8-diazaspiro[4.5]decan-2-one, 2 g of triethylamine and 10 ml N,N-dimethylformamide is stirred at 50° for 16 hours. The mixture is cooled to room temperature and 150 ml of water is added with stirring The aqueous layer is decanted from the residue which adheres to the walls of the flask. The residue is washed with 100 ml water following by 100 ml diethyl ether. The residue is dissolved in a minimum amount of 10% (v/v) methanol-dichloromethane and the resulting solution is filtered through 25 g silica gel with 150 ml of 10% (v/v) methanol-dichloromethane. Evaporation of the filtrate followed by crystallization with diethyl ether affords 2.35 g of 8-[2-(3-indolyl)ethyl]-1-oxa-3,8-diazaspiro[4.5]decan-2-one, mp 183°–186° (d).

Similarly prepared are:
(from 3-methyl-1-oxa-3,8-diazaspiro[4.5]decan-2-one),
3-methyl-8-[2-(3-indolyl)ethyl]-1-oxa-3,8-diazaspiro[4.5]decan-2-one, mp 187°–189° (d);
(from 3-ethyl-1-oxa-3,8-diazaspiro[4.5]decan-2-one), 3-ethyl-8-[2-(3-indolyl)ethyl]-1-oxa-3,8-diazaspiro[4.5]decan-2-one, a foam;
(from 3-i-propyl-1-oxa-3,8-diazaspiro[4.5]decan-2-one),
3-i-propyl-8-[2-(3-indolyl)ethyl]-1-oxa-3,8-diazaspiro[4.5]decan-2-one, mp 137°–138°;
(from 3-propyl-1-oxa-3,8-diazaspiro[4.5]decan-2-one),
3-propyl-8-[2-(3-indolyl)ethyl]-1-oxa-3,8-diazaspiro[4.5]decan-2-one, mp 141°–143°;
(from 3-butyl-1-oxa-3,8-diazaspiro[4.5]decan-2-one,
3-butyl-8-[2-(3-indolyl)ethyl]-1-oxa-3,8-diazaspiro[4.5]decan-2-one, mp 129°–131°;
(from 3-benzyl-1-oxa-3,8-diazaspiro[4.5]decan-2-one),
3-benzyl-8-[2-(3-indolyl)ethyl]-1-oxa-3,8-diazaspiro[4.5]decan-2-one, a foam;
(from 3-(2-phenethyl)-1-oxa-3,8-diazaspiro[4.5]decan-2-one),
3-(2-phenethyl)-8-[2-(3-indolyl)ethyl]-1-oxa-3,8-diazaspiro[4.5]decan-2-one, mp 143°–145°;
(from 3-phenyl-1-oxa-3,8-diazaspiro[4.5]decan-2-one),
3-phenyl-8-[2-(3-indolyl)ethyl]-1-oxa-3,8-diazaspiro[4.5]decan-2-one;
(from 4-methyl-1-oxa-3,8-diazaspiro[4.5]decan-2-one),
4-methyl-8-[2-(3-indolyl)ethyl]-1-oxa-3,8-diazaspiro[4.5]decan-2-one, mp 199°–203° (d);
(from 4-ethyl-1-oxa-3,8-diazaspiro[4.5]decan-2-one),
4-ethyl-8-[2-(3-indolyl)ethyl]-1-oxa-3,8-diazaspiro[4.5]decan-2-one;
(from 4,4-dimethyl-1-oxa-3,8-diazaspiro[4.5]decan-2-one),
4,4-dimethyl-8-[2-(3-indolyl)ethyl]-1-oxa-3,8-diazaspiro[4.5]decan-2-one;
(from 4-phenyl-1-oxa-3,8-diazaspiro[4.5]decan-2-one),
4-phenyl-8-[2-(3-indolyl)ethyl]-1-oxa-3,8-diazaspiro[4.5]decan-2-one, mp 184°–187° (d);
(from 4-benzyl-1-oxa-3,8-diazaspiro[4.5]decan-2-one),
4-benzyl-8-[2-(3-indolyl)ethyl]-1-oxa-3,8-diazaspiro[4.5]decan-2-one, mp 238°–240° (d);
(from 1-oxa-3,8-diazaspiro[4.5]decan-2-one and 6-methoxy-3-(2-bromoethyl)indole),
8-[2-(6-methoxy-3-indolyl)ethyl]-1-oxa-3,8-diazaspiro[4.5]decan-2-one, mp 173°–176°; and
(from 3-methyl-1-oxa-3,8-diazaspiro[4.5]decan-2-one and 6-methoxy-2-(2-bromoethyl)indole),
3-methyl-8-[2-(6-methoxy-3-indolyl)ethyl]-1-one-3,8-diazaspiro[4.5]decan-2-one, mp 199°–208° (d).

EXAMPLE 2

A mixture of 3.64 g 1-methyl-3-(2-hydroxyethyl)indole, 18 g triphenyl phosphite methiodide and 60 ml dry N,N-dimethylformamide is left at room temperature for 2.5 hours. The excess iodinating reagent is decomposed by addition of 5 ml of methanol. After 30 minutes, the mixture is poured into 500 ml dichloromethane and the resulting mixture is washed successively with 100 ml portions of 5% aqueous sodium thiosulfate, 5% aqueous sodium hydroxide and water. The dichloromethane is removed by vaccum evaporation (bath temperature 40°) leaving an N,N-dimethylformamide solution of 1-methyl-3-(2-iodoethyl)indole. To this solution are added 1.9 g 1-oxa-3,8-diazaspiro[4.5]decan-2-one, and 2 g triethylamine. The mixture is stirred at 50° for 16 hours. The contents of the flask are cooled to room temperature and 150 ml water is added with stirring. The aqueous layer is decanted from the residue which adheres to the walls of the flask. The residue is washed with another 150 ml water, taken up with 1 N hydrochloric acid and extracted with dichloromethane. The aqueous layer is basified with 15% sodium hydroxide solution and the liberated base is extracted with three 100 ml portions of dichloromethane. Evaporation of the combined extract gives a residue which is recrystalized from diethyl ether to give 1 g 8-[2-(1-methyl-3-indolyl)ethyl]-1-oxa-3,8-diazaspiro[4.5]decan-2-one, mp 158°–161°.

Similarly prepared is following:
(from 3-methyl-1-oxa-3,8-diazaspiro[4.5]decan-2-one),
3-methyl-8-[2-(1-methyl-3-indolyl)ethyl]-1-oxa-3,8-diazaspiro[4.5]decan-2-one, mp 105°–106°.

EXAMPLE 3

To a solution of 2 g 8-[2-(3-indolyl)ethyl]-1-oxa-3,8-diazaspiro[4.5]decan-2-one in 20 ml i-propyl alcohol is added sufficient 3% methanolic hydrogen chloride to make the solution acid to litmus. Addition of 250 ml diethyl ether followed by filtration affords 1.89 g 8-[2-(3-indolyl)ethyl]-1-oxa-3,8-diazaspiro[4.5]decan-2-one hydrochloride, mp 249°–254° (d).

Similarly prepared are the following:
3-methyl-[2-(3-indolyl)ethyl]-1-oxa-3,8-diazaspiro[4.5]decan-2-one hydrochloride, mp 238°–242° (d);
3-ethyl-[2-(3-indolyl)ethyl]-1-oxa-3,8-diazaspiro[4.5]decan-2-one hydrochloride, mp 238°–244° (d);
3-i-propyl-[2-(3-indolyl)ethyl]-1-oxa-3,8-diazaspiro[4.5]decan-2-one hydrochloride, mp 248°–252° (d);
3-propyl-[2-(3-indolyl)ethyl]-1-oxa-3,8-diazaspiro[4.5]decan-2-one hydrochloride, mp 227°–230° (d);
3-butyl-[2-(3-indolyl)ethyl]-1-oxa-3,8-diazaspiro[4.5]decan-2-one hydrochloride, mp 190°–192° (d);
3-phenyl-[2-(3-indolyl)ethyl]-1-oxa-3,8-diazaspiro[4.5]decan-2-one hydrochloride;
3-benzyl-[2-(3-indolyl)ethyl]-1-oxa-3,8-diazaspiro[4.5]decan-2-one hydrochloride, mp 225°–230° (d);
3-(2-phenethyl)-[2-(3-indolyl)ethyl]-1-oxa-3,8-diazaspiro[4.5]decan-2-one hydrochloride, mp 232°–238° (d);
4-methyl-[2-(3-indolyl)ethyl]-1-oxa-3,8-diazaspiro[4.5]decan-2-one hydrochloride, mp 242°–247° (d);
4,4-dimethyl-[2-(3-indolyl)ethyl]-1-oxa-3,8-diazaspiro[4.5]decan-2-one hydrochloride;
4-phenyl-[2-(3-indolyl)ethyl]-1-oxa-3,8-diazaspiro[4.5]decan-2-one hydrochloride, mp 187°–190° (d);
4-benzyl-[2-(3-indolyl)ethyl]-1-oxa-3,8-diazaspiro[4.5]decan-2-one hydrochloride, mp 255°–260° (d);
8-[2-(1-methyl-3-indolyl)ethyl]-1-oxa-3,8-diazaspiro[4.5]decan-2-one hydrochloride, mp 163°–165° (d);
3-methyl-8-[2-(1-methyl-3-indolyl)ethyl]-1-oxa-3,8-diazaspiro[4.5]decan-2-one hydrochloride, mp 265°–275° (d);
8-[2-(6-methoxy-3-indolyl)ethyl]-1-oxa-3,8-diazaspiro[4.5]decan-2-one-hydrochloride, mp 261°–266° (d); and
3-methyl-8-[2-(6-methoxy-3-indolyl)ethyl]-1-oxa-3,8-diazaspiro[4.5]decan-2-one hydrochloride, mp 240°–245° (d).

While the present invention has been described with reference to specific embodiments thereof, it should be understood by those skilled in the art that various changes may be made and equivalents may be substituted without departing from the true spirit and scope of the invention. In addition, many modifications can be made to adapt a particular situation, material or composition of matter, process, process step or steps or objective to the spirit of this invention without departing from its essential teachings.

What is claimed is:

1. A compound chosen from those represented by the formula wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

2. The compound of claim 1 wherein $R^1$ is hydrogen, methyl, ethyl, i-propyl, n-propyl, or n-butyl and $R^6$ and $R^7$ are hydrogen.

3. The compound in accordance with claim 2 wherein $R^1$ is methyl.

4. A method for relieving the symptoms of hypertension which comprises administering to an individual afflicted with such, an anti-hypertensive effective amount of a compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

5. A pharmaceutical composition useful for relieving the symptoms of hypertension which comprises a pharmaceutically acceptable carrier and an anti-hypertensive effective amount of the compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

6. A method useful for inhibiting the effects of allergic reaction which comprises administering an anti-allergic effective amount of a compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

7. A pharmaceutical composition useful for inhibiting the effects of allergic reactions which comprises a pharmaceutically acceptable carrier and an anti-allergic effective amount of a compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

8. A method for the treatment of vasospastic disorders which comprises administering an anti-vasospastic effective amount of the compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

9. A pharmaceutical composition useful for treating vaso spastic disorders which comprises a pharmaceutically acceptable carrier and an anti-vasospastic effective amount of the compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

10. A method for treatment of migraine which comprises administering an anti-migraine effective amount of the compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

11. A pharmaceutical composition useful for treating migraine which comprises a pharmaceutically acceptable carrier and an anti-migraine effective amount of a compound of the formula:

wherein $R^1$ is $C_1$ to $C_6$ alkyl and $R^6$ and $R^7$ are the same or different and are hydrogen or $C_1$ to $C_6$ alkoxy and the pharmaceutically acceptable, non-toxic salts thereof.

* * * * *